(12) United States Patent

He

(10) Patent No.: US 12,636,338 B2
(45) Date of Patent: May 26, 2026

(54) CHINESE HERBAL MEDICINE ANTI-VIRUS ARECA NUT PRODUCT AND PREPARATION METHOD THEREOF, AND ARECA NUT ADDITIVE AGENT

(71) Applicant: Changde Jizhi Biological Technology Co., Ltd, Changde (CN)

(72) Inventor: Xinqiao He, Changde (CN)

(73) Assignee: Changde Jizhi Biological Technology Co., Ltd, Changde (CN)

( * ) Notice: Subject to any disclaimer, the term of this patent is extended or adjusted under 35 U.S.C. 154(b) by 301 days.

(21) Appl. No.: 18/450,460

(22) Filed: Aug. 16, 2023

(65) Prior Publication Data

US 2024/0139273 A1 May 2, 2024

(30) Foreign Application Priority Data

Nov. 1, 2022 (CN) .......................... 202211372447.2

(51) Int. Cl.
*A61K 36/889* (2006.01)
*A61K 45/06* (2006.01)
(52) U.S. Cl.
CPC ............ *A61K 36/889* (2013.01); *A61K 45/06* (2013.01)

(58) Field of Classification Search
None
See application file for complete search history.

(56) References Cited

U.S. PATENT DOCUMENTS

2012/0201909 A1* 8/2012 Sanabria ................. A61P 39/00
424/727

* cited by examiner

*Primary Examiner* — Susan Hoffman
(74) *Attorney, Agent, or Firm* — Hemisphere Law, PLLC

(57) ABSTRACT

An areca nut product and preparation method thereof, and an areca nut additive agent are provided. The areca nut product is prepared from areca nuts, citric acid, mature vinegar, chitosan, active zinc oxide, monazite calcined distilled water, bovine bone protein peptide, lipase, isomaltooligo-saccharide, soybean lecithin, ginseng, atractylodes macro-cephala, poria cocos, liquorice, astragalus, notoginseng, tangerine peel, folium eucommiae, citronella grass, and mucor. Experimental tests shows that the areca nut product of the disclosure has a good antiviral effect, and the areca nut product has good preventive and therapeutic effects on oral diseases; compared with ordinary areca nut products, carci-nogenic study has shown that carcinogenicity of the areca nut product of the disclosure has significantly reduced.

6 Claims, No Drawings

CHINESE HERBAL MEDICINE ANTI-VIRUS ARECA NUT PRODUCT AND PREPARATION METHOD THEREOF, AND ARECA NUT ADDITIVE AGENT

TECHNICAL FIELD

The disclosure relates to the field of biopharmaceutical technology, in particular to a Chinese herbal medicine anti-virus areca nut product and preparation method thereof, and an areca nut additive agent.

BACKGROUND

The medical community believes that frequent chewing of an areca nut can cause oral ulcers, gum degeneration, and submucosal fibrosis, and then lead to oral cancer. Arecamine and arecoline in the areca nut have potential carcinogenicity, and carcinogenic substances in the areca nut include areca alkaloids, areca nut tannins, areca nut specific nitrosamines and reactive oxygen species.

Areca nut contains over 20 trace elements in which 11 trace elements are essential for the human body. Areca seeds contain 0.3%-0.6% of the total alkaloids, mainly including arecoline, and a small amount of arecaidine, guvacoline, isoguvacine, arecolidine and homoarecoline, all of which are concentrated with tannin acids. The betel nut further contains tannins, fats, mannitol, galactose, sucrose, catechin, epicatechin, leucoanthocyanidin, areca red pigment, saponins, and dimers, trimers, tetramer of a variety of procyanidin.

As reported by Chinese drug regulatory department, 225 drugs in China contain the areca nut. Traditional medicine practitioners believe that the areca nut has effects of "killing parasites, removing food retention, lowering qi and removing stagnation, promoting diuresis and eliminating dampness", and the areca nut has been used to treat infections caused by parasites such as tapeworms, hookworms, roundworms, pinworms, and ginger worms.

As a traditional food, the areca nut is deeply loved by the masses and has formed a market of hundreds of billions of yuan. Due to the problems of oral health hazards and carcinogenesis, on Sep. 17, 2021, the national radio and television administration of China issued a notice to stop using radio and television and network audio-visual programs to promote the areca nut and related products.

The areca nut can be made into a beneficial areca product by retaining beneficial substances and removing harmful substances. It is significant to develop a Chinese herbal medicine areca nut product and an areca nut additive agent with antiviral functions. By improving existing processes and formulations, the areca nut product can kill various harmful bacteria, inactivate various viruses, and prevent and treat various oral diseases. By swallowing juice of the areca nut product, it can also play a role in preventing cancer. Chewing the betel nut product in moderation can ensure that the mucosa does not become inflamed, achieving purposes of non-drug prevention and disease treatment, which has huge market value and important significance.

SUMMARY

In view of the above reasons, the disclosure provides a novel areca nut product. The areca nut product is prepared from areca nuts, citric acid, mature vinegar, chitosan, active zinc oxide, monazite calcined distilled water, bovine bone protein peptide, lipase, isomaltooligosaccharide, soybean lecithin, ginseng, atractylodes macrocephala, poria cocos, liquorice, astragalus, notoginseng, tangerine peel, folium eucommiae, citronella grass, and mucor. Experimental tests shows that the areca nut product of the disclosure has a good antiviral effect, and the areca nut product has good preventive and therapeutic effects on oral diseases; compared with ordinary areca nut products, carcinogenic study has shown that carcinogenicity of the areca nut product of the disclosure has significantly reduced.

The disclosure is achieved by following technical solutions.

An areca nut product is provided, and the areca nut product is prepared from areca nuts, citric acid, mature vinegar, chitosan, active zinc oxide, monazite calcined distilled water, bovine bone protein peptide, lipase, isomaltooligosaccharide, soybean lecithin, ginseng, atractylodes macrocephala, poria cocos, liquorice, astragalus, notoginseng, tangerine peel, folium eucommiae, citronella grass, and mucor.

In the areca nut product, the citric acid is 100~200 parts by weight, the mature vinegar is 300~500 parts by weight, the chitosan is 20~40 parts by weight, the active zinc oxide is 5~15 parts by weight, the monazite calcined distilled water is 5~15 parts by weight, the bovine bone protein peptide is 40~50 parts by weight, the lipase is 50~70 parts by weight, the isomaltooligosaccharide is 150~300 parts by weight, the soybean lecithin is 50~75 parts by weight, the ginseng is 50~80 parts by weight, the atractylodes macrocephala is 200~300 parts by weight, the poria cocos is 100~150 parts by weight, the liquorice is 300~400 parts by weight, the astragalus is 150~250 parts by weight, the notoginseng is 90~130 parts by weight, the tangerine peel is 250~300 parts by weight, the folium eucommiae is 350~450 parts by weight, the citronella grass is 350~400 parts by weight, and the mucor is 150~200 parts by weight.

In an embodiment, the citric acid is 150 parts by weight, the mature vinegar is 400 parts by weight, the chitosan is 30 parts by weight, the active zinc oxide is 10 parts by weight, the monazite calcined distilled water is 10 parts by weight, the bovine bone protein peptide is 45 parts by weight, the lipase is 60 parts by weight, the isomaltooligosaccharide is 225 parts by weight, the soybean lecithin is 60 parts by weight, the ginseng is 65 parts by weight, the atractylodes macrocephala is 250 parts by weight, the poria cocos is 125 parts by weight, the liquorice is 350 parts by weight, the astragalus is 200 parts by weight, the notoginseng is 110 parts by weight, the tangerine peel is 275 parts by weight, the folium eucommiae is 400 parts by weight, the citronella grass is 375 parts by weight, and the mucor is 175 parts by weight.

A preparation method of the areca nut product is provided, which includes:

step 1: mixing the citric acid with water 10 times a weight of the citric acid to obtain a citric acid solution, heating the citric acid solution to 100 Celsius degrees (° C.), cooling down the citric acid solution to 50° C., placing the citric acid solution in a barrel, immersing the areca nuts in the citric acid solution and adding the mature vinegar into the citric acid solution, immersing the areca nuts in the citric acid solution for 12~16 hours, and taking out and drying the areca nuts to obtain dried areca nuts;

step 2: cleaning traditional Chinese medicines including the ginseng, the atractylodes macrocephala, the poria cocos, the liquorice, the astragalus, the notoginseng, the tangerine peel, the folium eucommiae, and the citronella grass to obtain cleaned traditional Chinese medicines, crushing the cleaned traditional Chinese medicines, steaming the cleaned traditional Chinese medicines after crushing in a steamer for 30 minutes to obtain steamed traditional Chinese medicines, drying the steamed traditional Chinese medicines after taking the steamed traditional Chinese medicines from the steamer, adding the isomaltooligosaccharide into the steamed traditional Chinese medicines for mixing evenly and adding the mucor into the steamed traditional Chinese medicines, and fermenting the steamed traditional Chinese medicines in a fermentation tank at a room temperature for 30 days, thereby obtaining fermented traditional Chinese medicines;

step 3: adding the bovine bone protein peptide, the chitosan, the lipase, the active zinc oxide, the soybean lecithin into the fermented traditional Chinese medicines, and adding the monazite calcined distilled water into the fermented traditional Chinese medicines for mixing evenly, thereby obtaining an additive agent; and step 4: cutting each of the dried areca nuts into two pieces, adding the additive agent according to a weight ratio of 10:1 between the dried areca nuts and the additive agent, evenly stirring the dried areca nuts and the additive agent evenly to obtain an areca nut pre-product, and drying the areca nut pre-product to obtain the areca nut product.

An application of the areca nut product in preparation of drugs for treating oral diseases is provided.

An application of the areca nut product in preparation of drugs for treating stomatitis is provided.

An application of the areca nut product in preparation of drugs for treating aphthous stomatitis is provided.

All raw materials described in disclosure are purchased from Shen Yao (Xianghe) Technology Co., Ltd.

The monazite calcined distilled water of the disclosure is prepared by: crushing the monazite to obtain a monazite powder, putting the monazite powder into a furnace with a temperature of 1800° C.~2000° C. to burn the monazite powder for 75~105 minutes to obtain a burned powder; cooling the burned powder to obtain a cooled power; and putting the cooled powder into a 800 mesh~1000 mesh cloth bag and distilling the cloth bag in a steam oven to obtain the monazite calcined distilled water.

In an embodiment, the monazite calcined distilled water of the disclosure is prepared by: crushing the monazite to obtain a monazite powder, putting the monazite powder into a furnace with a temperature of 2000° C. to burn the monazite powder for 90 minutes to obtain a burned powder; cooling the burned powder to obtain a cooled power; and putting the cooled powder into a 1000-mesh cloth bag and distilling the cloth bag in a steam oven to obtain the monazite calcined distilled water.

The lipase (also referred to as glyceride hydrolase) of the disclosure belongs to carboxyl ester hydrolase and can hydrolyze triglyceride into glycerol and fatty acid step by step. Lipase exists in the tissues of animals, plants and microorganisms (such as mildew, bacteria, etc.) containing fat. The lipase includes phosphatase, sterolase, and carboxylesterase. Fatty acids are widely used in food, medicine, leather, daily use, chemical industry and so on.

The mucor of the disclosure is also known as black mold or long mold. Mucor is a large genus of fungi belonging to mucor family of mucor order of zygomycetes class of zygomycetes subphylum. The mucor propagates with sporangiospores and zygospores. The Mucor exists in environments such as soil, feces, grass, and air. The mucor grows well under conditions of high temperature, high humidity, and poor ventilation.

The active zinc oxide (ZnO) of the disclosure has a particle size between 1~100 nm and is a new type of highly functional fine inorganic product in the 21st century. The active zinc oxide exhibits many special properties, such as non-mobility, fluorescence, piezoelectricity, absorption and scattering of ultraviolet rays, etc. By utilizing the properties of the active zinc oxide in light, electricity, magnetism, sensitivity, and other aspects, gas sensors, phosphors, varistors, and ultraviolet shielding materials, image recording materials, piezoelectric materials, piezoresistors, high-efficiency catalysts, magnetic materials, plastic films and others can be manufactured.

The isomaltooligosaccharide (IMO) of the disclosure meets the standard of Chinese light industry.

The mature vinegar of the disclosure is commercially available. The bovine bone protein peptide of the disclosure is known as bovine bone collagen peptide, which is commercially available.

The disclosure uses the mature vinegar and citric acid to process the areca nuts for removing toxic components, then the fermented traditional Chinese medicine, active components, and the monazite calcined distilled water are mixed evenly with the processed areca nuts to obtain the areca nut product.

DETAILED DESCRIPTION OF EMBODIMENTS

In order to make the purpose, technical solutions, and advantages of the disclosure clearer, the following will provide a further detailed explanation of the disclosure in conjunction with specific embodiments. It should be understood that these descriptions are only illustrative and not intended to limit a scope of the disclosure. In addition, in the following explanation, the description of well-known structures and techniques has been omitted to avoid unnecessary confusion with the concepts of the disclosure.

Embodiment 1

An areca nut product is prepared from: 1000 grams (g) of citric acid, 3000 g of mature vinegar, 200 g of chitosan, 50 g of active zinc oxide, 50 g of monazite calcined distilled water, 400 g of bovine bone protein peptide, 500 g of lipase, 1500 g of isomaltooligosaccharide, 500 g of soybean lecithin, 500 g of ginseng, 2000 g of atractylodes macrocephala, 1000 g of poria cocos, 3000 g of liquorice, 1500 g of astragalus, 900 g of notoginseng, 2500 g of tangerine peel, 3500 g of folium eucommiae, 3500 g of citronella grass, and 1500 g of mucor.

A preparation method of the areca nut product is provided, which includes:

step 1: mixing the citric acid with water 10 times a weight of the citric acid to obtain a citric acid solution, heating the citric acid solution to 100° C., cooling down the citric acid solution to 50° C., placing the citric acid solution in a barrel, immersing the areca nuts in the citric acid solution and adding the mature vinegar into the citric acid solution, immersing the areca nuts in the citric acid solution for 12 hours, and taking out and drying the areca nuts to obtain dried areca nuts;

step 2: cleaning traditional Chinese medicines including the ginseng, the atractylodes macrocephala, the poria cocos, the liquorice, the astragalus, the notoginseng, the tangerine peel, the folium eucommiae, and the citronella grass to obtain cleaned traditional Chinese medicines, crushing the cleaned traditional Chinese medicines, steaming the cleaned traditional Chinese medicines after crushing in a steamer for 30 minutes to obtain steamed traditional Chinese medicines, drying the steamed traditional Chinese medicines after taking the steamed traditional Chinese medicines from the steamer, adding the isomaltooligosaccharide into the steamed traditional Chinese medicines for mixing evenly and adding the mucor into the steamed traditional Chinese medicines, and fermenting the steamed traditional Chinese medicines in a fermentation tank at a room temperature for 30 days, thereby obtaining fermented traditional Chinese medicines;

step 3: adding the bovine bone protein peptide, the chitosan, the lipase, the active zinc oxide, the soybean lecithin into the fermented traditional Chinese medicines, and adding the monazite calcined distilled water into the fermented traditional Chinese medicines for mixing evenly, thereby obtaining an additive agent; and step 4: cutting each of the dried areca nuts into two pieces, adding the additive agent according to a weight ratio of 10:1 between the dried areca nuts and the additive agent, evenly stirring the dried areca nuts and the additive agent evenly to obtain an areca nut pre-product, and drying the areca nut pre-product to obtain the areca nut product.

Specifically, the monazite calcined distilled water of the disclosure is prepared by: crushing the monazite to obtain a monazite powder, putting the monazite powder into a furnace with a temperature of 2000° C. to burn the monazite powder for 90 minutes to obtain a burned powder; cooling the burned powder to obtain a cooled power; and putting the cooled powder into a 1000-mesh cloth bag and distilling the cloth bag in a steam oven to obtain the monazite calcined distilled water.

Embodiment 2

An areca nut product is prepared from: 2000 g of citric acid, 5000 g of mature vinegar, 400 g of chitosan, 150 g of active zinc oxide, 150 g of monazite calcined distilled water, 500 g of bovine bone protein peptide, 700 g of lipase, 3000 g of isomaltooligosaccharide, 750 g of soybean lecithin, 800 g of ginseng, 3000 g of atractylodes macrocephala, 1500 g of poria cocos, 4000 g of liquorice, 2500 g of astragalus, 1300 g of notoginseng, 3000 g of tangerine peel, 4500 g of folium eucommiae, 4000 g of citronella grass, and 2000 g of mucor.

A preparation method of the areca nut product is provided, which includes:

step 1: mixing the citric acid with water 10 times a weight of the citric acid to obtain a citric acid solution, heating the citric acid solution to 100° C., cooling down the citric acid solution to 50° C., placing the citric acid solution in a barrel, immersing the areca nuts in the citric acid solution and adding the mature vinegar into the citric acid solution, immersing the areca nuts in the citric acid solution for 16 hours, and taking out and drying the areca nuts to obtain dried areca nuts;

step 2: cleaning traditional Chinese medicines including the ginseng, the atractylodes macrocephala, the poria cocos, the liquorice, the astragalus, the notoginseng, the tangerine peel, the folium eucommiae, and the citronella grass to obtain cleaned traditional Chinese medicines, crushing the cleaned traditional Chinese medicines, steaming the cleaned traditional Chinese medicines after crushing in a steamer for 30 minutes to obtain steamed traditional Chinese medicines, drying the steamed traditional Chinese medicines after taking the steamed traditional Chinese medicines from the steamer, adding the isomaltooligosaccharide into the steamed traditional Chinese medicines for mixing evenly and adding the mucor into the steamed traditional Chinese medicines, and fermenting the steamed traditional Chinese medicines in a fermentation tank at a room temperature for 30 days, thereby obtaining fermented traditional Chinese medicines;

step 3: adding the bovine bone protein peptide, the chitosan, the lipase, the active zinc oxide, the soybean lecithin into the fermented traditional Chinese medicines, and adding the monazite calcined distilled water into the fermented traditional Chinese medicines for mixing evenly, thereby obtaining an additive agent; and step 4: cutting each of the dried areca nuts into two pieces, adding the additive agent according to a weight ratio of 10:1 between the dried areca nuts and the additive agent, evenly stirring the dried areca nuts and the additive agent evenly to obtain an areca nut pre-product, and drying the areca nut pre-product to obtain the areca nut product.

Specifically, the monazite calcined distilled water of the disclosure is prepared by: crushing the monazite to obtain a monazite powder, putting the monazite powder into a furnace with a temperature of 2000° C. to burn the monazite powder for 90 minutes to obtain a burned powder; cooling the burned powder to obtain a cooled power; and putting the cooled powder into a 1000-mesh cloth bag and distilling the cloth bag in a steam oven to obtain the monazite calcined distilled water.

Embodiment 3

An areca nut product is prepared from: 1500 g of citric acid, 4000 g of mature vinegar, 300 g of chitosan, 100 g of active zinc oxide, 100 g of monazite calcined distilled water, 450 g of bovine bone protein peptide, 600 g of lipase, 2250 g of isomaltooligosaccharide, 600 g of soybean lecithin, 650 g of ginseng, 2500 g of atractylodes macrocephala, 1250 g of poria cocos, 3500 g of liquorice, 2000 g of astragalus, 1100 g of notoginseng, 2750 g of tangerine peel, 4000 g of folium eucommiae, 3750 g of citronella grass, and 1750 g of mucor.

A preparation method of the areca nut product is provided, which includes:

step 1: mixing the citric acid with water 10 times a weight of the citric acid to obtain a citric acid solution, heating the citric acid solution to 100° C., cooling down the citric acid solution to 50° C., placing the citric acid solution in a barrel, immersing the areca nuts in the citric acid solution and adding the mature vinegar into the citric acid solution, immersing the areca nuts in the citric acid solution for 14 hours, and taking out and drying the areca nuts to obtain dried areca nuts;

step 2: cleaning traditional Chinese medicines including the ginseng, the atractylodes macrocephala, the poria cocos, the liquorice, the astragalus, the notoginseng, the tangerine peel, the folium eucommiae, and the citronella grass to obtain cleaned traditional Chinese medicines, crushing the cleaned traditional Chinese medicines, steaming the cleaned traditional Chinese medicines after crushing in a steamer for 30 minutes to obtain steamed traditional Chinese medicines, drying the steamed traditional Chinese medicines after taking the steamed traditional Chinese medicines from the steamer, adding the isomaltooligosaccharide into the steamed traditional Chinese medicines for mixing evenly and adding the mucor into the steamed traditional Chinese medicines, and fermenting the steamed traditional Chinese medicines in a fermentation tank at a room temperature for 30 days, thereby obtaining fermented traditional Chinese medicines;

step 3: adding the bovine bone protein peptide, the chitosan, the lipase, the active zinc oxide, the soybean lecithin into the fermented traditional Chinese medicines, and adding the monazite calcined distilled water into the fermented traditional Chinese medicines for mixing evenly, thereby obtaining an additive agent; and step 4: cutting each of the dried areca nuts into two pieces, adding the additive agent according to a weight ratio of 10:1 between the dried areca nuts and the additive agent, evenly stirring the dried areca nuts and the additive agent evenly to obtain an areca nut pre-product, and drying the areca nut pre-product to obtain the areca nut product.

Specifically, the monazite calcined distilled water of the disclosure is prepared by: crushing the monazite to obtain a monazite powder, putting the monazite powder into a furnace with a temperature of 2000° C. to burn the monazite powder for 90 minutes to obtain a burned powder; cooling the burned powder to obtain a cooled power; and putting the cooled powder into a 1000-mesh cloth bag and distilling the cloth bag in a steam oven to obtain the monazite calcined distilled water.

Embodiment 4

An areca nut product is prepared from: 1200 g of citric acid, 3500 g of mature vinegar, 250 g of chitosan, 65 g of active zinc oxide, 60 g of monazite calcined distilled water, 420 g of bovine bone protein peptide, 550 g of lipase, 1750 g of isomaltooligosaccharide, 550 g of soybean lecithin, 580 g of ginseng, 2300 g of atractylodes macrocephala, 1150 g of poria cocos, 3300 g of liquorice, 1750 g of astragalus, 950 g of notoginseng, 2750 g of tangerine peel, 3750 g of folium eucommiae, 3650 g of citronella grass, and 1650 g of mucor.

A preparation method of the areca nut product is provided, which includes:

step 1: mixing the citric acid with water 10 times a weight of the citric acid to obtain a citric acid solution, heating the citric acid solution to 100° C., cooling down the citric acid solution to 50° C., placing the citric acid solution in a barrel, immersing the areca nuts in the citric acid solution and adding the mature vinegar into the citric acid solution, immersing the areca nuts in the citric acid solution for 14 hours, and taking out and drying the areca nuts to obtain dried areca nuts;

step 2: cleaning traditional Chinese medicines including the ginseng, the atractylodes macrocephala, the poria cocos, the liquorice, the astragalus, the notoginseng, the tangerine peel, the folium eucommiae, and the citronella grass to obtain cleaned traditional Chinese medicines, crushing the cleaned traditional Chinese medicines, steaming the cleaned traditional Chinese medicines after crushing in a steamer for 30 minutes to obtain steamed traditional Chinese medicines, drying the steamed traditional Chinese medicines after taking the steamed traditional Chinese medicines from the steamer, adding the isomaltooligosaccharide into the steamed traditional Chinese medicines for mixing evenly and adding the mucor into the steamed traditional Chinese medicines, and fermenting the steamed traditional Chinese medicines in a fermentation tank at a room temperature for 30 days, thereby obtaining fermented traditional Chinese medicines;

step 3: adding the bovine bone protein peptide, the chitosan, the lipase, the active zinc oxide, the soybean lecithin into the fermented traditional Chinese medicines, and adding the monazite calcined distilled water into the fermented traditional Chinese medicines for mixing evenly, thereby obtaining an additive agent; and step 4: cutting each of the dried areca nuts into two pieces, adding the additive agent according to a weight ratio of 10:1 between the dried areca nuts and the additive agent, evenly stirring the dried areca nuts and the additive agent evenly to obtain an areca nut pre-product, and drying the areca nut pre-product to obtain the areca nut product.

Specifically, the monazite calcined distilled water of the disclosure is prepared by: crushing the monazite to obtain a monazite powder, putting the monazite powder into a furnace with a temperature of 2000° C. to burn the monazite powder for 90 minutes to obtain a burned powder; cooling the burned powder to obtain a cooled power; and putting the cooled powder into a 1000-mesh cloth bag and distilling the cloth bag in a steam oven to obtain the monazite calcined distilled water.

Embodiment 5

An areca nut product is prepared from: 1850 g of citric acid, 4850 g of mature vinegar, 385 g of chitosan, 140 g of active zinc oxide, 130 g of monazite calcined distilled water, 485 g of bovine bone protein peptide, 680 g of lipase, 2850 g of isomaltooligosaccharide, 710 g of soybean lecithin, 780 g of ginseng, 2800 g of atractylodes macrocephala, 1400 g of poria coco s, 3800 g of liquorice, 2350 g of astragalus, 1200 g of notoginseng, 2800 g of tangerine peel, 4400 g of folium eucommiae, 3900 g of citronella grass, and 1900 g of mucor.

A preparation method of the areca nut product is provided, which includes:

step 1: mixing the citric acid with water 10 times a weight of the citric acid to obtain a citric acid solution, heating the citric acid solution to 100° C., cooling down the citric acid solution to 50° C., placing the citric acid solution in a barrel, immersing the areca nuts in the citric acid solution and adding the mature vinegar into the citric acid solution, immersing the areca nuts in the citric acid solution for 15 hours, and taking out and drying the areca nuts to obtain dried areca nuts;

step 2: cleaning traditional Chinese medicines including the ginseng, the atractylodes macrocephala, the poria cocos, the liquorice, the astragalus, the notoginseng, the tangerine peel, the folium eucommiae, and the citronella grass to obtain cleaned traditional Chinese medicines, crushing the cleaned traditional Chinese medicines, steaming the cleaned traditional Chinese medicines after crushing in a steamer for 30 minutes to obtain steamed traditional Chinese medicines, drying the steamed traditional Chinese medicines after taking the steamed traditional Chinese medicines from the steamer, adding the isomaltooligosaccharide into the steamed traditional Chinese medicines for mixing evenly and adding the mucor into the steamed traditional Chinese medicines, and fermenting the steamed traditional Chinese medicines in a fermentation tank at a room temperature for 30 days, thereby obtaining fermented traditional Chinese medicines;

step 3: adding the bovine bone protein peptide, the chitosan, the lipase, the active zinc oxide, the soybean lecithin into the fermented traditional Chinese medicines, and adding the monazite calcined distilled water into the fermented traditional Chinese medicines for mixing evenly, thereby obtaining an additive agent; and step 4: cutting each of the dried areca nuts into two pieces, adding the additive agent according to a weight ratio of 10:1 between the dried areca nuts and the additive agent, evenly stirring the dried areca nuts and the additive agent evenly to obtain an areca nut pre-product, and drying the areca nut pre-product to obtain the areca nut product.

Specifically, the monazite calcined distilled water of the disclosure is prepared by: crushing the monazite to obtain a monazite powder, putting the monazite powder into a furnace with a temperature of 2000° C. to burn the monazite powder for 90 minutes to obtain a burned powder; cooling the burned powder to obtain a cooled power; and putting the cooled powder into a 1000-mesh cloth bag and distilling the cloth bag in a steam oven to obtain the monazite calcined distilled water.

Comparative Example 1

An areca nut product is prepared from: 300 g of chitosan, 100 g of active zinc oxide, 100 g of monazite calcined distilled water, 450 g of bovine bone protein peptide, 600 g of lipase, 2250 g of isomaltooligosaccharide, 600 g of soybean lecithin, 650 g of ginseng, 2500 g of atractylodes macrocephala, 1250 g of poria cocos, 3500 g of liquorice, 2000 g of astragalus, 1100 g of notoginseng, 2750 g of tangerine peel, 4000 g of folium eucommiae, 3750 g of citronella grass, and 1750 g of mucor.

A preparation method of the areca nut product is provided, which includes:

step 1: drying fresh areca nuts to obtain dried areca nuts for standby;

step 2: cleaning traditional Chinese medicines including the ginseng, the atractylodes macrocephala, the poria cocos, the liquorice, the astragalus, the notoginseng, the tangerine peel, the folium eucommiae, and the citronella grass to obtain cleaned traditional Chinese medicines, crushing the cleaned traditional Chinese medicines, steaming the cleaned traditional Chinese medicines after crushing in a steamer for 30 minutes to obtain steamed traditional Chinese medicines, drying the steamed traditional Chinese medicines after taking the steamed traditional Chinese medicines from the steamer, adding the isomaltooligosaccharide into the steamed traditional Chinese medicines for mixing evenly and adding the mucor into the steamed traditional Chinese medicines, and fermenting the steamed traditional Chinese medicines in a fermentation tank at a room temperature for 30 days, thereby obtaining fermented traditional Chinese medicines;

step 3: adding the bovine bone protein peptide, the chitosan, the lipase, the active zinc oxide, the soybean lecithin into the fermented traditional Chinese medicines, and adding the monazite calcined distilled water into the fermented traditional Chinese medicines for mixing evenly, thereby obtaining an additive agent; and step 4: cutting each of the dried areca nuts into two pieces, adding the additive agent according to a weight ratio of 10:1 between the dried areca nuts and the additive agent, evenly stirring the dried areca nuts and the additive agent evenly to obtain an areca nut pre-product, and drying the areca nut pre-product to obtain the areca nut product.

Specifically, the monazite calcined distilled water of the disclosure is prepared by: crushing the monazite to obtain a monazite powder, putting the monazite powder into a furnace with a temperature of 2000° C. to burn the monazite powder for 90 minutes to obtain a burned powder; cooling the burned powder to obtain a cooled power; and putting the cooled powder into a 1000-mesh cloth bag and distilling the cloth bag in a steam oven to obtain the monazite calcined distilled water.

Comparative Example 2

An areca nut product is prepared from: 1500 g of citric acid, 4000 g of mature vinegar, 300 g of chitosan, 100 g of active zinc oxide, 450 g of bovine bone protein peptide, 600 g of lipase, 2250 g of isomaltooligosaccharide, 600 g of soybean lecithin, 2500 g of atractylodes macrocephala, 2000 g of astragalus, 1100 g of notoginseng, 2750 g of tangerine peel, 4000 g of folium eucommiae, 3750 g of citronella grass, and 1750 g of mucor.

A preparation method of the areca nut product, which includes:

step 1: mixing the citric acid with water 10 times a weight of the citric acid to obtain a citric acid solution, heating the citric acid solution to 100° C., cooling down the citric acid solution to 50° C., placing the citric acid solution in a barrel, immersing the areca nuts in the citric acid solution and adding the mature vinegar into the citric acid solution, immersing the areca nuts in the citric acid solution for 14 hours, and taking out and drying the areca nuts to obtain dried areca nuts;

step 2: cleaning traditional Chinese medicines including atractylodes macrocephala, astragalus, notoginseng, tangerine peel, folium eucommiae, and citronella grass to obtain cleaned traditional Chinese medicines, crushing the cleaned traditional Chinese medicines, steaming the cleaned traditional Chinese medicines after crushing in a steamer for 30 minutes to obtain steamed traditional Chinese medicines, drying the steamed traditional Chinese medicines after taking the steamed traditional Chinese medicines from the steamer, adding the isomaltooligosaccharide into the steamed traditional Chinese medicines for mixing evenly and adding the mucor into the steamed traditional Chinese medicines, and fermenting the steamed traditional Chinese medicines in a fermentation tank at a room temperature for 30 days, thereby obtaining fermented traditional Chinese medicines;

step 3: adding bovine bone protein peptide, chitosan, lipase, active zinc oxide, soybean lecithin into the fermented traditional Chinese medicines for mixing evenly, thereby obtaining an additive agent; and step 4: cutting each of the dried areca nuts into two pieces, adding the additive agent according to a weight ratio of 10:1 between the dried areca nuts and the additive agent, evenly stirring the dried areca nuts and the additive agent evenly to obtain an areca nut pre-product, and drying the areca nut pre-product to obtain the areca nut product.

Specifically, the monazite calcined distilled water of the disclosure is prepared by: crushing the monazite to obtain a monazite powder, putting the monazite powder into a furnace with a temperature of 2000° C. to burn the monazite powder for 90 minutes to obtain a burned powder; cooling the burned powder to obtain a cooled power; and putting the cooled powder into a 1000-mesh cloth bag and distilling the cloth bag in a steam oven to obtain the monazite calcined distilled water.

Test 1: Virus Inactivation Test

The areca nut products prepared in the embodiment 1~5 and comparative examples 1~2 are performed with a virus inactivation test.

The test method refers to the 2020 version of the "Technical Specifications for Disinfection"-2.1. 1. 10. 7.

Test virus: H1N1 influenza virus, H5N1 influenza virus, H7N9 influenza virus. Host cell: Madin-Darby canine kidney (MDCK) cell.

Test drug concentration (calculated based on the areca nut products): 500 mg/ml, a solvent for the test is physiological saline (each of the areca nut products are crushed to 100 mesh and added to the physiological saline, thereby obtaining a suspension). The action time of the drug (i.e., the suspension) on the virus is 3 hours.

Test results are shown in TABLES 1~3.

TABLE 1

| | Inhibitory effect of the disclosure on the H1N1 influenza virus | | | |
|---|---|---|---|---|
| Group | Viral titer 1 g TCID 50/mL | 50% cell infective dose TCID 50/mL | Killing log value | Inactivation rate % |
| Embodiment 1 | 2.37 | 32.47 | 4.24 | 99.00% |
| Embodiment 2 | 2.29 | 32.98 | 4.47 | 99.00% |
| Embodiment 3 | 1.70 | 23.75 | 5.74 | 99.00% |
| Embodiment 4 | 2.25 | 31.83 | 4.45 | 99.00% |
| Embodiment 5 | 2.13 | 31.26 | 4.63 | 99.00% |
| Comparative example 1 | 4.75 | 8937.00 | 1.46 | 90.26% |
| Comparative example 2 | 5.24 | 9668.72 | 1.25 | 87.15% |

*The cells in the negative control group grew well, and the test results met all the conditions specified in the evaluation.

TABLE 2

| | Inhibitory effect of the disclosure on the H5N1 influenza virus | | | |
|---|---|---|---|---|
| Group | Viral titer 1 g TCID 50/mL | 50% cell infective dose TCID 50/mL | Killing log value | Inactivation rate % |
| Embodiment 1 | 2.47 | 32.72 | 4.17 | 99.00% |
| Embodiment 2 | 2.34 | 33.24 | 4.39 | 99.00% |
| Embodiment 3 | 1.75 | 24.64 | 5.66 | 99.00% |
| Embodiment 4 | 2.32 | 32.12 | 4.38 | 99.00% |
| Embodiment 5 | 2.16 | 31.75 | 4.57 | 99.00% |
| Comparative example 1 | 4.84 | 8871.26 | 1.39 | 89.14% |
| Comparative example 2 | 5.29 | 9739.41 | 1.19 | 81.77% |

*The cells in the negative control group grew well, and the test results met all the conditions specified in the evaluation.

TABLE 3

| | Inhibitory effect of the disclosure on the H7N9 influenza virus | | | |
|---|---|---|---|---|
| Group | Viral titer 1 g TCID 50/mL | 50% cell infective dose TCID 50/mL | Killing log value | Inactivation rate % |
| Embodiment 1 | 2.31 | 32.06 | 4.17 | 99.00% |
| Embodiment 2 | 2.24 | 32.72 | 4.38 | 99.00% |
| Embodiment 3 | 1.65 | 23.65 | 5.66 | 99.00% |

TABLE 3-continued

| | Inhibitory effect of the disclosure on the H7N9 influenza virus | | | |
|---|---|---|---|---|
| Group | Viral titer 1 g TCID 50/mL | 50% cell infective dose TCID 50/mL | Killing log value | Inactivation rate % |
| Embodiment 4 | 2.23 | 31.47 | 4.37 | 99.00% |
| Embodiment 5 | 2.07 | 30.84 | 4.52 | 99.00% |
| Comparative example 1 | 4.68 | 8919.75 | 1.41 | 88.36% |
| Comparative example 2 | 5.17 | 9589.35 | 1..05 | 82.43% |

*The cells in the negative control group grew well, and the test results met all the conditions specified in the evaluation.

Test conclusion: the above tests indicate that the areca nut products of the disclosure have good antiviral effects and have a good inhibitory effect on viruses in the oral cavity, with an inactivation rate of 99%; and the significant decrease in antiviral effect of the areca nut products of the comparative example 1 and comparative example 2 fully demonstrates the significance of the disclosure.

Test 2: Carcinogenic Study on Oral Cavity of Rats

Test animal: specific pathogen free (SPF) healthy golden hamster with a body weight of 95~105 g.

Test method: golden hamsters are randomly divided into a normal control group, a dimethyl benzoanthracene group, a group of embodiment 3, a group of comparative example 1, and a group of comparative example 2. For the normal control group, the golden hamsters of the normal control group do not undergo any treatment. For the group of embodiment 3, the group of comparative example 1, and the group of comparative example 2, the golden hamsters are anesthetized with ether, and cheek pouches on both sides of the golden hamsters are abraded with fine sandpaper, then the areca nut products prepared in the embodiment 3, comparative example 1, and comparative example 2 are taken and placed in the cheek pouches; the dosages of the areca nut products are given until the cheek pouches are filled, and the areca nut products are chewed by the golden hamster; and the areca nut products prepared in the embodiment 3, comparative example 1, and comparative example 2 are administered to the golden hamsters once a week for 18 weeks. For the dimethylbenzoanthracene group, the golden hamsters of the dimethylbenzoanthracene group are administered 0.1 mL of dimethylbenzoanthracene at a concentration of 5 g/L in both cheek pouches, and the dimethylbenzoanthracene are administered once every 2 days for 18 consecutive weeks. After the administration of the dimethylbenzoanthracene and the areca nut products are finished, changes of cheek pouches of golden hamsters of each group are observed with naked eyes, the golden hamsters of all groups are killed, their cheek pouches on both sides are taken and the cheek pouches are fixed with 40 g/L paraformaldehyde, ethanol and xylene of different volume fractions are used to dehydrate and transparentize the cheek pouches step by step, then the cheek pouches are embedded in paraffin and the cheek pouches in paraffin are cut into slices, the slices are pasted on glass slides, and the glass slides containing the slices are baked in an oven at 60° C. for 2 hours for standby. After baking, xylene is used to dewax the slices to obtain dewaxed slices, and different volume fractions of ethanol are used to dehydrate the dewaxed slices step by step, thereby obtaining dehydrated slices. Then, hematoxylin eosin (HE) staining and micronucleus staining are performed on the dehydrated slices, stained slices are seal with neutral gum, a microscope is used to observe the stained slices and the stained slice are photographed, thereby determining whether there are pathological changes in the cheek pouches of golden hamsters in each group (Note: This test method is implemented by referring to existing methods, and the technical effect of the technical solution of the disclosure is determined through this test method).

Test results are shown in TABLE 4

TABLE 4

Histological comparison of cheek pouches of golden hamsters

| Group | Number of animals | Histological comparison (HE staining, ×20) |
|---|---|---|
| Normal control group | 10 | a |
| Dimethyl benzoanthracene group | 10 | d |
| Group of embodiment 3 | 10 | b |
| Group of comparative example 1 | 10 | c |
| Group of comparative example 2 | 10 | c |

Note: a and b indicate that cells are arranged regularly and have polarity; c and d indicate that cells are in disorder, unclear hierarchy and extensive infiltration of cancer cells.

Test conclusion: the above test indicates that the areca nut product of the disclosure has less damage to cheek pouch cells of the golden hamster, and the cheek pouch cell are arranged regularly and have polarity, and there is almost no cancer cells. However, for the group of comparative example 1 and the group of comparative example 2, the arrangement of cheek pouch cells is disordered and unclear, with a large number of cancer cells infiltrating. This fully demonstrates that the areca nut product of the disclosure is safe and significantly reduces carcinogenicity.

The above are only some embodiments of the disclosure. It should be pointed out that for ordinary of those skill in this field, several improvements and modifications can be made without departing from the principles of the disclosure. These improvements and modifications should be within the scope of protection of the disclosure.

What is claimed is:

1. A preparation method of an areca nut product, comprising:

step 1: mixing citric acid with water 10 times a weight of the citric acid to obtain a citric acid solution, heating the citric acid solution to 100 Celsius degrees (° C.), cooling down the citric acid solution to 50° C., placing the citric acid solution in a barrel, immersing areca nuts in the citric acid solution and adding vinegar into the citric acid solution, immersing the areca nuts in the citric acid solution for 12~16 hours, and taking out and drying the areca nuts to obtain dried areca nuts;

step 2: cleaning a mixture comprising ginseng, atractylodes macrocephala, poria cocos, liquorice, astragalus, notoginseng, tangerine peel, folium eucommiae, and citronella grass to obtain a cleaned mixture, crushing the cleaned mixture, steaming the cleaned mixture after crushing in a steamer for 30 minutes to obtain a steamed mixture, drying the steamed mixture after taking the steamed mixture from the steamer, adding isomaltooligosaccharide into the steamed mixture for mixing evenly and adding mucor into the steamed mixture, and fermenting the steamed mixture in a fermentation tank at a room temperature for 30 days, thereby obtaining a fermented mixture;

step 3: adding bovine bone collagen peptide, chitosan, lipase, zinc oxide, soybean lecithin into the fermented mixture, and adding monazite calcined distilled water into the fermented mixture for mixing evenly, thereby obtaining an additive agent, wherein the zinc oxide has a particle size in a range of 1 nanometer (nm) to 100 nm;

wherein the monazite calcined distilled water is prepared by: crushing monazite to obtain a monazite powder, putting the monazite powder into a furnace with a temperature of 1800° C.~2000° C. to burn the monazite powder for 75~105 minutes to obtain a burned powder; cooling the burned powder to obtain a cooled powder; and putting the cooled powder into a 800 mesh~1000 mesh cloth bag and distilling the cloth bag in a steam oven to obtain distillation steam to thereby obtain the monazite calcined distilled water; and step 4: cutting each of the dried areca nuts into two pieces, adding an additive agent according to a weight ratio of 10:1 between the dried areca nuts and the additive agent, evenly stirring the dried areca nuts and the additive agent to obtain an areca nut pre-product, and drying the areca nut pre-product to obtain the areca nut product.

2. The preparation method of the areca nut product as claim in claim 1, wherein a duration of immersing the areca nuts in the citric acid solution is 12 hours.

3. The preparation method of the areca nut product as claim in claim 1, wherein a duration of immersing the areca nuts in the citric acid solution is 16 hours.

4. The preparation method of the areca nut product as claim in claim 1, wherein a duration of immersing the areca nuts in the citric acid solution is 14 hours.

5. The preparation method of the areca nut product as claim in claim 1, wherein a duration of immersing the areca nuts in the citric acid solution is 15 hours.

6. A preparation method of an areca nut product, comprising:

step 1, mixing citric acid with water 10 times a weight of the citric acid to obtain a citric acid solution, heating the citric acid solution to 100 Celsius degrees (° C.), cooling down the citric acid solution to 50° C., placing the citric acid solution in a barrel, immersing areca nuts in the citric acid solution and adding vinegar into the citric acid solution, immersing the areca nuts in the citric acid solution for 12~16 hours, and taking out and drying the areca nuts to obtain dried areca nuts;

step 2, cleaning a mixture comprising ginseng, atractylodes macrocephala, poria cocos, liquorice, astragalus, notoginseng, tangerine peel, folium eucommiae, and citronella grass to obtain a cleaned mixture, crushing the cleaned mixture, steaming the cleaned mixture after crushing in a steamer for 30 minutes to obtain a steamed mixture, drying the steamed mixture after taking the steamed mixture from the steamer, adding isomaltooligosaccharide into the steamed mixture for mixing evenly and adding mucor into the steamed mixture, and fermenting the steamed mixture in a fermentation tank at a room temperature for 30 days, thereby obtaining a fermented mixture;

step 3, adding bovine bone collagen peptide, chitosan, lipase, zinc oxide, soybean lecithin into the fermented mixture;

preparing monazite calcined distilled water, comprising:

crushing monazite to obtain a monazite powder, and putting the monazite powder into a furnace with a temperature of 2000° C. to burn the monazite powder for 90 minutes to obtain a burned powder;

cooling the burned powder to obtain a cooled powder; and putting the cooled powder into a 1000-mesh cloth bag and distilling the cloth bag in a steam oven to obtain distillation steam to thereby obtain the monazite calcined distilled water; and adding the monazite calcined distilled water into the fermented mixture for mixing evenly, thereby obtaining an additive agent, wherein the active zinc oxide has a particle size in a range of 1 nm to 100 nm; and step 4, cutting each of the dried areca nuts into two pieces, adding an additive agent according to a weight ratio of 10:1 between the dried areca nuts and the additive agent, evenly stirring the dried areca nuts and the additive agent to obtain an areca nut pre-product, and drying the areca nut pre-product to obtain the areca nut product.

\* \* \* \* \*